(12) United States Patent
Dubois et al.

(10) Patent No.: US 9,512,051 B2
(45) Date of Patent: Dec. 6, 2016

(54) CROSS METATHESIS PROCESS

(71) Applicant: ARKEMA FRANCE, Colombes (FR)

(72) Inventors: Jean-Luc Dubois, Millery (FR); Jean-Luc Couturier, Lyons (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/654,663

(22) PCT Filed: Jan. 7, 2014

(86) PCT No.: PCT/FR2014/050012
§ 371 (c)(1),
(2) Date: Jun. 22, 2015

(87) PCT Pub. No.: WO2014/106724
PCT Pub. Date: Jul. 10, 2014

(65) Prior Publication Data
US 2015/0344416 A1    Dec. 3, 2015

(30) Foreign Application Priority Data
Jan. 7, 2013   (FR) .................................... 13 50103

(51) Int. Cl.
*C07C 6/04* (2006.01)
*C07C 227/04* (2006.01)
*C07C 253/30* (2006.01)

(52) U.S. Cl.
CPC .............. *C07C 6/04* (2013.01); *C07C 227/04* (2013.01); *C07C 253/30* (2013.01)

(58) Field of Classification Search
None
See application file for complete search history.

(56) References Cited

U.S. PATENT DOCUMENTS

| | | | |
|---|---|---|---|
| 2009/0048459 A1* | 2/2009 | Tupy | C10G 45/00 554/146 |
| 2010/0168453 A1 | 7/2010 | Dubois | |
| 2011/0224454 A1 | 9/2011 | Dubois | |
| 2011/0300590 A1 | 12/2011 | Dubois | |
| 2013/0116458 A1 | 5/2013 | Couturier et al. | |

FOREIGN PATENT DOCUMENTS

| | | |
|---|---|---|
| FR | 2 912 741 A1 | 8/2008 |
| FR | 2 938 533 A1 | 5/2010 |

(Continued)

OTHER PUBLICATIONS

International Search Report (PCT/ISA/210) mailed on Feb. 27, 2014, by the French Patent Office as the International Searching Authority for International Application No. PCT/FR2014/050012.

*Primary Examiner* — Yate K Cutliff
(74) *Attorney, Agent, or Firm* — Buchanan Ingersoll & Rooney P.C.

(57) ABSTRACT

A process for the synthesis of an unsaturated product by cross metathesis between a first unsaturated compound having at least 8 carbon atoms and a second unsaturated compound having less than 8 carbon atoms, the first unsaturated compound being capable of producing an unsaturated coproduct comprising more than 14 carbon atoms, by homo-metathesis, said process including at least one production phase which includes: feeding a reactor with the first unsaturated compound; feeding the reactor with the second unsaturated compound; feeding the reactor with at least a first metathesis catalysts, then feeding the reactor with at least a second metathesis catalyst; withdrawing a product stream arising from the reactor; the turnover number of the first catalyst being higher than the turnover number of the second catalyst so as to achieve the same target degree of conversion of the first unsaturated compound.

21 Claims, 4 Drawing Sheets

(56) References Cited

FOREIGN PATENT DOCUMENTS

| FR | 2 941 694 A1 | 8/2010 |
| FR | 2 959 742 A1 | 11/2011 |
| WO | WO 2008/104722 A2 | 9/2008 |
| WO | WO 2011/138051 A1 | 11/2011 |

* cited by examiner

CROSS METATHESIS PROCESS

FIELD OF THE INVENTION

The present invention relates to a cross metathesis process for the production of an unsaturated product such as an unsaturated nitrile-ester or nitrile-acid.

TECHNICAL BACKGROUND

The polyamides industry uses an entire range of monomers formed from diamines and from diacids, from lactams, and especially from w-amino acids. These monomers are defined by the length of the methylene chain $(-CH_2)_n$ separating two amide functions $-CO-NH-$. These monomers are conventionally manufactured via the chemical synthesis route using, as raw materials, $C_2$ to $C_4$ olefins, cycloalkanes or benzene, which are hydrocarbons derived from fossil sources. For example, $C_2$ olefins are used to manufacture the $C_9$ amino acid used in nonanoic acid; $C_4$ olefins are used to manufacture hexamethylenediamine; laurolactam and caprolactam are manufactured from cycloalkanes; adipic acid, Nylon 6 and Nylon 6,6 are manufactured from benzene.

Current developments in environmental matters are leading, in the fields of energy and chemistry, to the exploitation of natural raw materials originating from a renewable source being favored. It is the reason why certain studies have been undertaken in order to industrially develop processes using fatty acids/esters as raw material for manufacturing these monomers.

Document FR 2912741 thus describes a process for the synthesis of an entire range of amino acids/esters from a natural long-chain fatty acid/ester, by subjecting the latter to a catalytic cross metathesis reaction with an unsaturated compound comprising a nitrile function, followed by hydrogenation.

Document FR 2938533 describes a process for the synthesis of ω-aminoalkanoic acids or esters thereof from natural unsaturated long-chain fatty acids, passing through an intermediate compound of w-unsaturated nitrile type, one of the variants of which implements, in the final phase, a cross metathesis of the ω-unsaturated nitrile with a compound of acrylate type.

Document FR 2941694 describes a variant of the above process, in which the intermediate compound is of the unsaturated dinitrile type.

These processes result, at the end of a step of hydrogenation of the nitrile function and of the double bond, in the manufacture of amino acids.

Finally, the object of document FR 2959742 is to improve the performance levels of processes which successively implement a cross metathesis and a hydrogenation.

In these processes, the cross metathesis reactions, generally carried out between an omega-unsaturated fatty nitrile and an acrylate, or between an omega-unsaturated fatty ester and acrylonitrile, result not only in the desired product which is a nitrile-ester, but also in products resulting from a homometathesis reaction of fatty substances, such as respectively dinitriles and diesters. By increasing the amounts of catalyst used, the reaction times and/or the ratios between the reagents, it is possible to convert these coproducts resulting from homometathesis into a nitrile-ester, but these solutions prove to be expensive and not very productive.

Furthermore, the products of the homometathesis reactions (diesters or dinitriles) are heavy, long-chain products which have limited applications, which are often unrelated to the desired industrial applications for the nitrile-esters.

There is therefore a real need to develop a process for the synthesis of an unsaturated fatty compound by cross metathesis (and in particular for the synthesis of a nitrile-ester/acid) in which the amount of coproducts resulting from the homometathesis reactions is reduced and which does not require excessive consumption of catalyst.

SUMMARY OF THE INVENTION

The invention relates firstly to a process for the synthesis of an unsaturated product by cross metathesis between a first unsaturated compound comprising at least 8 carbon atoms and a second unsaturated compound comprising less than 8 carbon atoms, the first unsaturated compound being capable of producing an unsaturated coproduct comprising more than 14 carbon atoms, by homometathesis, said process comprising at least one production phase which comprises:
  feeding a reactor with the first unsaturated compound;
  feeding the reactor with the second unsaturated compound;
  feeding the reactor with at least a first metathesis catalyst, then feeding the reactor with at least a second metathesis catalyst;
  withdrawing a product stream arising from the reactor;
  the turnover number of the first catalyst being higher than the turnover number of the second catalyst so as to achieve the same target degree of conversion of the first unsaturated compound, the turnover numbers of the catalysts being determined under temperature, pressure, stoichiometry and reagent concentration conditions identical to those of the production phase.

According to one embodiment, the target degree of conversion ($ODC_{TA}$) is from 30% to 95%, preferably from 40% to 90%, in particular from 50% to 80%, more particularly from 60% to 75%.

According to one embodiment, the production phase is semi-batch, and preferably comprises successively:
(1) feeding the reactor with all of the first unsaturated compound and a first part of the second unsaturated compound, before starting up the reaction;
(2) gradually feeding the reactor with a second part of the second unsaturated compound and with the first catalyst;
(3) gradually feeding the reactor with a third part of the second unsaturated compound and with the second catalyst.

According to one embodiment:
the first unsaturated compound has the formula:

$$R_1-CH=CH-(CH_2)_n-R_2; \quad (I)$$

the second unsaturated compound has the formula:

$$R_3-CH=CH-R_4; \quad (II)$$

the unsaturated product has the formula:

$$R_4-CH=CH-(CH_2)_n-R_2; \quad (III)$$

the unsaturated coproduct has the formula:

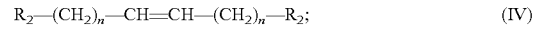
$$R_2-(CH_2)_n-CH=CH-(CH_2)_n-R_2; \quad (IV)$$

$R_1$ representing a hydrogen atom or an alkyl or alkenyl radical comprising from 1 to 8 carbon atoms; $R_2$ representing $COOR_5$ or CN or CHO or $CH_2OH$ or $CH_2Cl$ or $CH_2Br$; $R_3$ and $R_4$ each representing a hydrogen atom or an alkyl radical comprising from 1 to 4 carbon atoms or $COOR_5$ or CN or CHO or $CH_2OH$ or $CH_2Cl$ or $CH_2Br$, $R_3$ and $R_4$ being identical or different and not comprising in total more than 6 carbon atoms; $R_5$ representing a hydrogen atom or an alkyl radical comprising from 1 to 4 carbon atoms; and n being an integer from 4 to 11.

According to one embodiment, the second unsaturated compound is an acrylate or preferably acrylonitrile, the first unsaturated compound is an acid, an unsaturated nitrile or an unsaturated ester, preferably chosen from methyl 9-decenoate, 9-decenenitrile, 10-undecenenitrile and methyl 10-undecenoate, the unsaturated product is an unsaturated nitrile-ester, nitrile-acid, dinitrile or diester, and the unsaturated coproduct is an unsaturated diester, dinitrile or diacid.

According to one embodiment, the metathesis reactions are carried out in the liquid phase, where appropriate in a solvent, and preferably result in the production of at least one unsaturated compound in gas form, more particularly preferably ethylene, in the reactor, the process comprising the continuous drawing off thereof from the reactor.

According to one embodiment, the degree of conversion of the first unsaturated compound at the end of the production phase is from 50% to 98%, preferably from 60% to 95%, more particularly preferably from 70% to 90%.

According to one embodiment, the process comprises a preliminary phase of selecting the first catalyst and the second catalyst from a set of possible catalysts, before the production phase.

According to one embodiment, the preliminary selection phase comprises:
- carrying out a reference process for each possible catalyst, each reference process comprising feeding the reactor with the first unsaturated compound, feeding the reactor with the second unsaturated compound and feeding the reactor with the catalyst, the temperature, pressure, stoichiometry and reagent concentration conditions for each reference process being identical to those used for the production phase;
- collecting the results of the reference processes, comprising measuring concentrations of chemical species in the reactor over time;
- choosing the first catalyst and the second catalyst according to the results of the reference processes.

According to one embodiment, the first catalyst is the catalyst which has the maximum turnover number in the reference process, for the same target degree of conversion of the first unsaturated compound.

According to one embodiment, the second catalyst is a catalyst for which, in the reference process, the absolute value of the derivative of the yield of the reaction in terms of unsaturated coproduct, as a function of the degree of conversion of the first unsaturated compound, determined at the degree of conversion of 1, is minimal.

According to one embodiment, the second catalyst is chosen, from the catalysts for which, in the reference process, the absolute value of the derivative of the yield of the reaction in terms of unsaturated coproduct, as a function of the degree of conversion of the first unsaturated compound, measured at the degree of conversion of 1, is minimal, as being the catalyst for which the turnover number in the reference process is at a maximum, for the same target degree of conversion of the first unsaturated compound.

According to one embodiment:
the number X is calculated at various instants of each reference process, said number X being defined by the following formula:

$$X = (UDC_2/2) \times (z/C_0 - UDC_1)/((1-ODC) \times UDC_1), \quad (1)$$

in which $C_0$ represents the number of moles of the first unsaturated compound in the reactor before the beginning of feeding with catalyst, ODC represents the degree of conversion of the first unsaturated compound at the instant under consideration, $UDC_1$ represents the yield of the reaction in terms of unsaturated product at the instant under consideration, $UDC_2$ represents the yield of the reaction in terms of unsaturated coproduct at the instant under consideration, and z represents the cumulative total number of moles of second unsaturated compound that are introduced into the reactor at the instant under consideration;

the number Y is calculated at various instants of each reference process, said number Y being defined by the following formula:

$$Y = (p \times \alpha(2+p)) \times (z/(C_0 \times UDC_1) - 1) + (2+2p) \times (1-ODC)/((2+p) \times UDC_1) \quad (2)$$

in which $C_0$, ODC, $UDC_1$ and z have the meaning above, p represents the absolute value (therefore positive value) of the derivative of the function $UDC_2(ODC)$ for a degree of conversion equal to 1, and α is $(2a/b) \times (C_0/C'_0)$, a representing the derivative of the function $UDC_1(ODC)$ for a degree of conversion equal to 0, b representing the derivative of the function $UDC_2(ODC)$ for a degree of conversion equal to 0 and $C'_0$ representing the number of moles of the second unsaturated compound in the reactor before the beginning of feeding with catalyst;

the function Y(X) is approximated by an equation $Y = \beta \times X$ or, preferably, by an equation $Y = \beta' \times X - \gamma'$, for the experimental data obtained for the highest conversions, i.e. those obtained beyond the conversion corresponding to the maximum yield in terms of unsaturated coproduct (β, β' and γ' necessarily being positive values);

the second catalyst is selected as being the catalyst for which the parameter β or β' is at a maximum.

According to one embodiment, the reactor is fed with first catalyst until the degree of conversion of the first unsaturated compound reaches a threshold value, said threshold value being from 30% to 90%, preferably from 40% to 80% and more particularly from 50% to 70%.

According to one embodiment, the reactor is fed with first catalyst for a duration equal to, or preferably greater than, a threshold duration, said threshold duration being that after which the degree of conversion of the first unsaturated compound is $ODC = ODC_{TH}$ and the yield in terms of unsaturated coproduct is $UDC_2 = UDC_{2TH}$ in a reference process, are connected by the equation $UDC_{2TH} = UDC^* \times (ODC_{TH} - 1)/(ODC^* - 1)$, where $UDC^*$ is the value of the yield in terms of unsaturated coproduct that is desired at the end of the production phase, and $ODC^*$ is the value of the degree of conversion of the first unsaturated compound that is desired at the end of the production phase, the reference process comprising feeding the reactor with the first unsaturated compound, feeding the reactor with the second unsaturated compound and feeding the reactor with the first catalyst, the temperature, pressure, stoichiometry and reagent concentration conditions for the reference process being identical to those used during the production phase.

According to one embodiment, the reactor is fed with first catalyst for a duration equal to, or preferably greater than, a threshold duration which is the duration after which, in a reference process, the second derivative of the turnover number of the first catalyst as a function of time is cancelled out, the reference process comprising feeding the reactor with the first unsaturated compound, feeding the reactor with the second unsaturated compound and feeding the reactor with the first catalyst, the temperature, pressure, stoichiometry and reagent concentration conditions for the reference process being identical to those used during the production phase.

According to one embodiment, the process comprises, before the production phase, a preliminary phase for determining the duration of introduction of the first catalyst, which comprises:

carrying out the reference process;

collecting the results of the reference process, comprising measuring concentrations of chemical species in the reactor over time; and calculating the duration of introduction of the first catalyst according to the results of the reference processes.

According to one embodiment, the first catalyst and/or the second catalyst are ruthenium-carbene catalysts, and are preferably chosen from the catalysts of formulae (A) and (B) below:

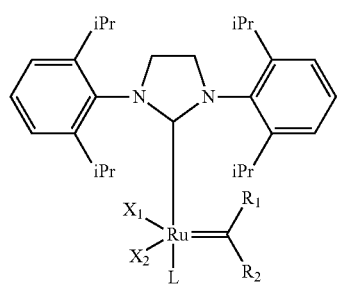

(A)

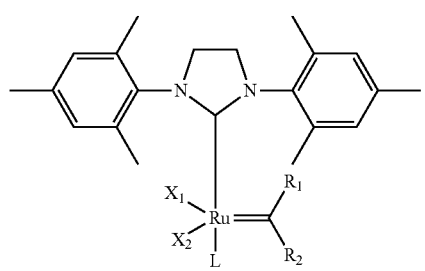

B in which $X_1$ et $X_2$ are anionic ligands, L is an electron-donating neutral ligand, and $R_1$ and $R_2$ represent H or a substituent containing from 1 to 20 carbon atoms of alkyl, alkenyl, alkynyl, aryl, alkoxy, alkenyloxy, alkynyloxy, aryloxy, alkoxycarbonyl, alkylthiol, arylthiol, alkylsulfonyl or alkylsulfinyl type; the substituent optionally containing groups of hydroxyl, thiol, thioether, ketone, aldehyde, ester, ether, amine, imine, amide, nitro, carboxylic acid, disulfide, carbonate, isocyanate, carbodiimide, carboalkoxy, carbamate or halogen type, $R_2$ preferably being bonded to L so as to form a chelating ligand.

According to one embodiment, the first catalyst and/or the second catalyst are chosen from the catalysts of formulae (A-1) to (A-10) and (B-1) to (B-5) below:

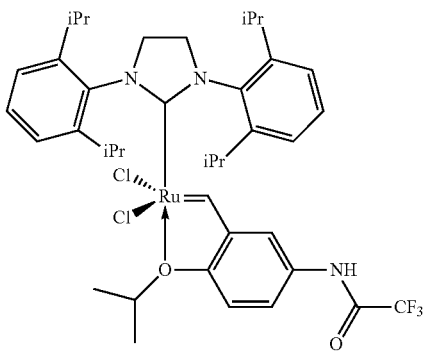

(A-1)

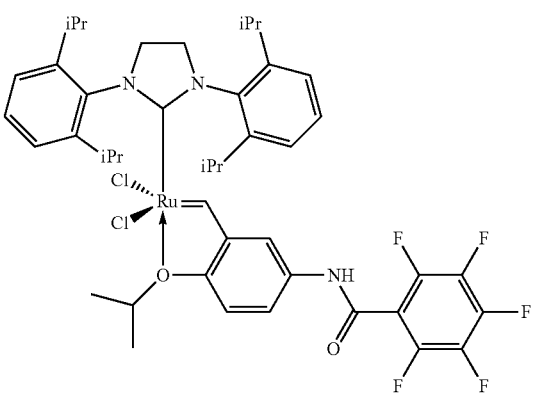

(A-2)

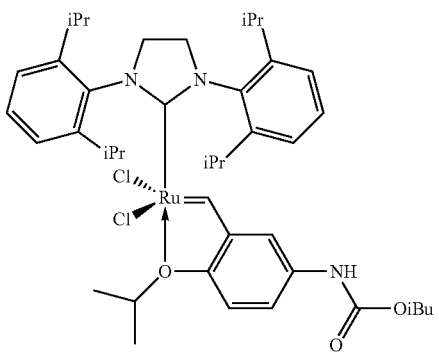

(A-3)

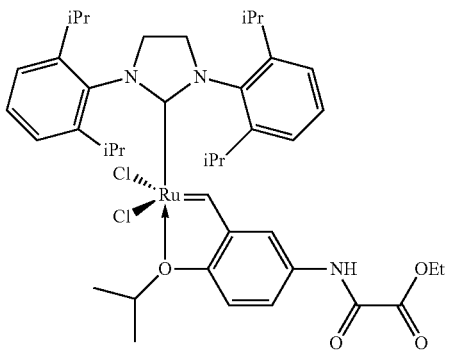

(A-4)

(A-5) 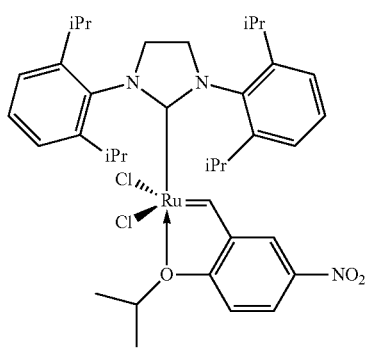
(A-6) 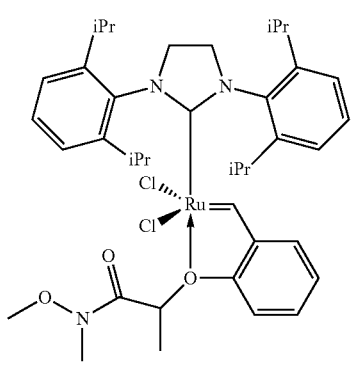
(A-7) 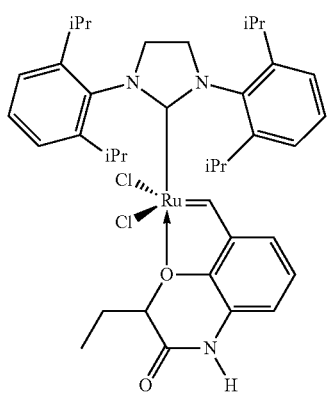
(A-8) 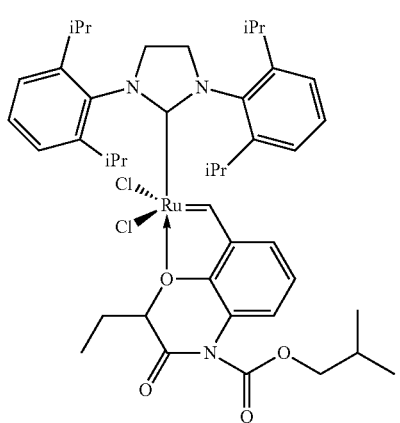
(A-9) 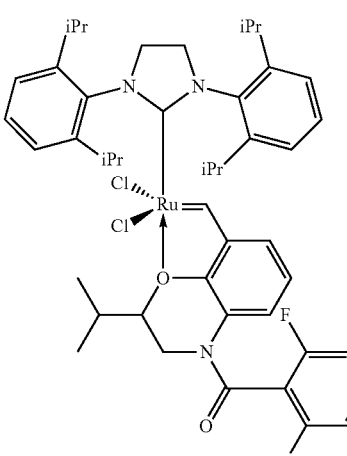
(A-10) 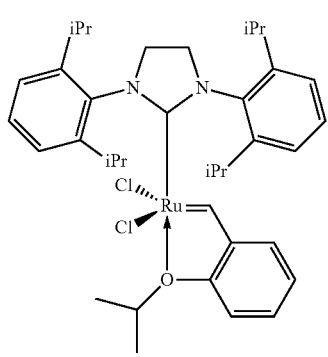
(B-1) 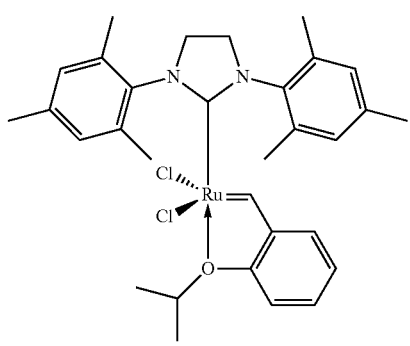
(B-2) 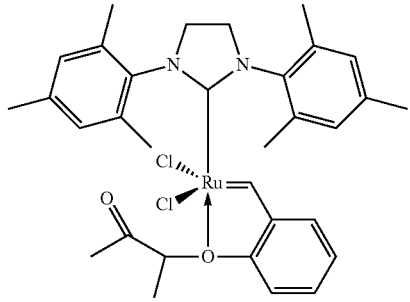

-continued

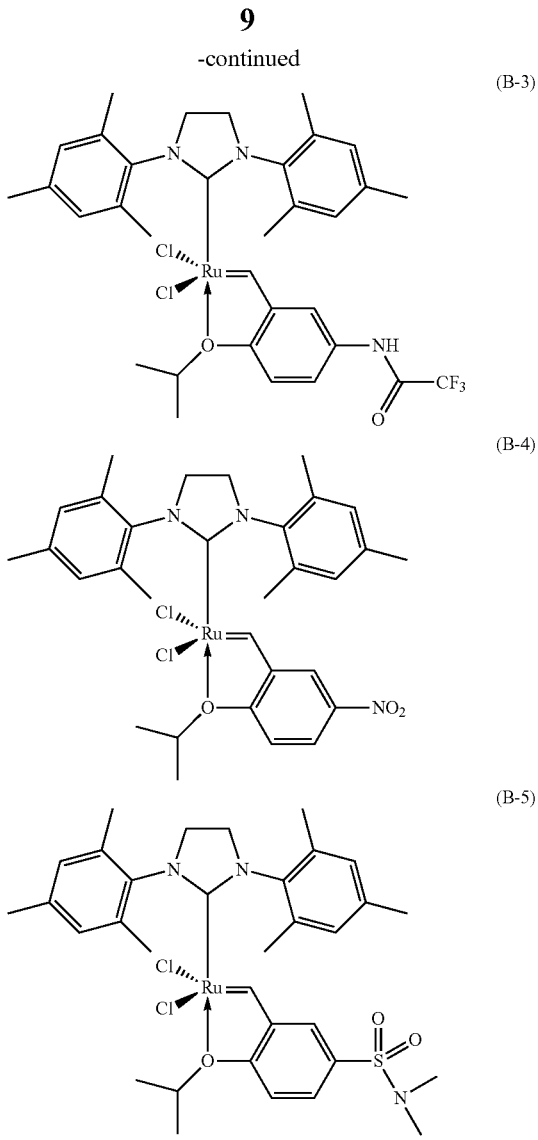

According to one embodiment, the first catalyst is a catalyst of formula (A) and the second catalyst is a catalyst of formula (B), or preferably the first catalyst is chosen from the catalysts of formulae (A-1) to (A-10) and the second catalyst is chosen from the catalysts of formulae (B-1) to (B-5).

The invention also relates to a process for the synthesis of an α,ω-aminoalkanoic acid or ester, comprising the synthesis of an unsaturated product according to the process above, which is an unsaturated nitrile-ester or nitrile-acid, and a reaction for hydrogenation thereof.

The present invention makes it possible to overcome the drawbacks of the prior art. It provides more particularly a process for the synthesis of an unsaturated fatty compound by cross metathesis (and in particular for the synthesis of a nitrile-ester/acid) in which the amount of coproducts resulting from the homometathesis reactions is reduced and the amount of catalyst consumed is also reduced.

The invention is based on the discovery that the use of at least two different catalysts, in a particular order, makes it possible to minimize the yield in terms of coproduct. The performance levels of the reaction are thus better than with a single catalyst or with a mixture of catalysts.

DESCRIPTION OF EMBODIMENTS OF THE INVENTION

Figure 1:
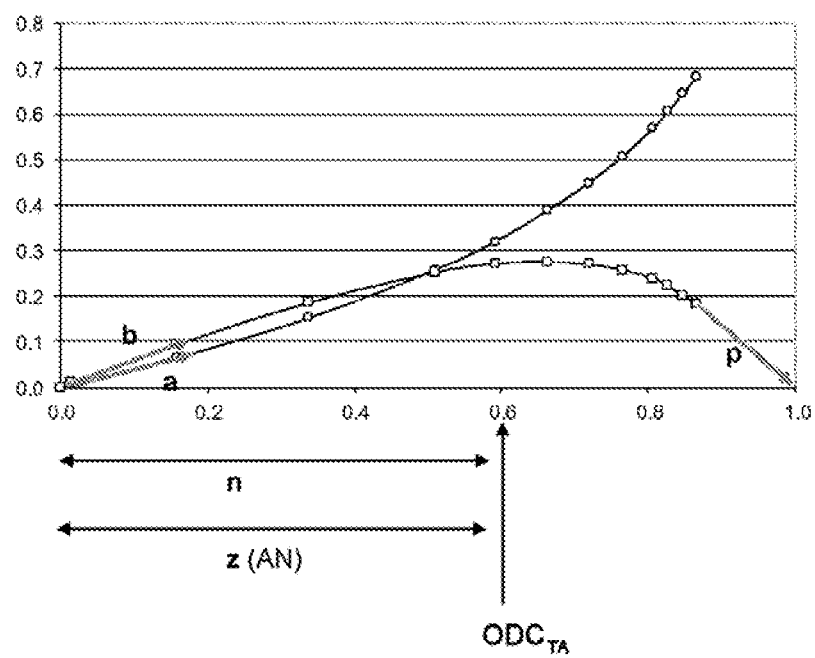
FIG. 1 is an illustration of the results collected during a reference process used in the context of the invention. The degree of conversion of the first unsaturated compound is given along the x-axis and the yield in terms of unsaturated product ($UDC_1$, points o) and of unsaturated coproduct ($UDC_2$, points □) is given along the y-axis. The target degree of conversion $ODC_{T4}$ for which the comparison with other catalysts is made is selected from the data collected for this figure.

The invention is now described in greater detail and in a nonlimiting manner in the description which follows.

Metathesis Reaction

The invention implements a metathesis reaction between an unsaturated fatty compound comprising at least 8 carbon atoms, called first unsaturated compound, and a functional or non-functional olefin comprising less than 8 carbon atoms, called second unsaturated compound.

The first unsaturated compound has the formula (I) $R_1$—CH=CH—$(CH_2)_n$—$R_2$ and the second unsaturated compound has the formula (II) $R_3$—CH=CH—$R_4$ with:
  $R_1$=H or alkyl or alkenyl radical comprising from 1 to 8 carbon atoms;
  $R_2$=$COOR_5$, CN, CHO, $CH_2OH$, $CH_2Cl$ or $CH_2Br$;
  $R_3$ and $R_4$=H, alkyl radical having from 1 to 4 carbon atoms, $COOR_5$, CN, CHO, $CH_2OH$, $CH_2Cl$ or $CH_2Br$, $R_3$ and $R_4$ being identical or different and $R_3+R_4$ do not comprise more than 6 carbon atoms;

$R_5$=H or alkyl radical comprising 1 to 4 carbon atoms;

n is between 4 and 11.

The reactions involved are:

cross metathesis between the compounds (I) and (II) giving the desired "unsaturated product" of formula (III) $R_4$—CH=CH—$(CH_2)_n$—$R_2$, and the compound of formula (V) $R_1$—CH=CH—$R_3$;

another cross metathesis between the compounds (I) and (II) giving the compound of formula (VI) $R_1$—CH=CH—$R_4$, and the compound of formula (VII) $R_3$—CH=CH—$(CH_2)_n$—$R_2$;

homometathesis of the compound (I), giving the "unsaturated coproduct" which is unwanted (or wanted in a lower amount), of formula (IV) $R_2$—$(CH_2)_n$—CH=CH—$(CH_2)_n$—$R_2$, and also the compound of formula (VIII) $R_1$—CH=CH—$R_1$;

cross homometathesis of the unsaturated coproduct of formula (IV) with the second unsaturated compound of formula (II), giving the desired unsaturated product of formula (III) and giving again the first unsaturated compound of formula (I).

There is generally no detectable homometathesis of the compound of formula (II) when use is made of acrylonitrile or acrylates.

In one preferred embodiment, the process involves the formation of a light product which can be removed from the reaction medium by distillation, thereby making it possible to shift the equilibria toward the formation of the desired products.

In the aforementioned, these light compounds are the compounds of formulae $R_1$—CH=CH—$R_3$ and $R_1$—CH=CH—$R_1$.

Preferably, the first unsaturated compound is an acid, a nitrile or an ester and the second unsaturated compound is acrylonitrile $CH_2$=CH—CN or an acrylate (for example a methyl or butyl acrylate), the unsaturated product is a nitrile-acid, an ester-acid, a diester, a dinitrile or a nitrile-ester, and the unsaturated coproduct is a diacid, a dinitrile or diester.

The first unsaturated compound may, for example, be an ester of formula $CH_2$=CH—$(CH_2)_n$—$COOCH_3$, the second unsaturated compound being acrylonitrile $CH_2$=CH—CN, in which case the unsaturated product is the compound NC—CH=CH—$(CH_2)_n$—$COOCH_3$, and the unsaturated coproduct is the diester $CH_3OOC$—$(CH_2)_n$—CH=CH—$(CH_2)_n$—$COOCH_3$. Ethylene $CH_2$=$CH_2$ is also produced both by cross metathesis and by homometathesis. It is this example which is retained for illustrating the remainder of the description below.

Besides the reactions of fatty esters with acrylonitrile, other preferred reactions are those of fatty nitriles with an acrylate, of fatty esters with an acrylate, of fatty nitriles with acrylonitrile, of fatty esters with a linear olefin, of fatty esters with a branched olefin, of fatty nitriles with a linear olefin and of fatty nitriles with a branched olefin.

The unsaturated product obtained by virtue of the process according to the invention can undergo subsequent hydrogenation, in a manner known per se.

Catalysts

The invention is based on the use of two successive catalysts.

Numerous catalysts exist for metathesis reactions. Mention may, for example, be made of the tungsten complexes developed by Schrock et al (*J. Am. Chem. Soc.* 108:2771, 1986) or Basset et al. (*Angew. Chem., Ed. Engl.* 31:628, 1992). More recently, catalysts termed Grubbs catalysts have emerged (see Grubbs et al., *Angew. Chem., Ed. Engl.* 34:2039, 1995 and *Organic Letters* 1:953, 1999) which are ruthenium-benzylidene complexes operating in homogeneous catalysis. Other studies have been carried out in order to produce immobilized catalysts, i.e. catalysts of which the active ingredient is that of the homogeneous catalyst, in particular ruthenium-carbene complexes immobilized on an inactive support.

The process according to the invention advantageously uses a metathesis catalyst of ruthenium-carbene type.

The ruthenium-carbene catalysts are preferably chosen from charged or uncharged catalysts of general formula:

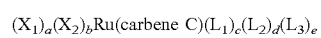

in which:

a, b, c, d and e are integers, which may be identical or different, with a and b equal to 0, 1 or 2; c, d and e equal to 0, 1, 2, 3 or 4;

$X_1$ and $X_2$, which may be identical or different, each represent a charged or uncharged and monochelating or polychelating ligand; by way of examples, mention may be made of halides, sulfate, carbonate, carboxylates, alcoholates, phenolates, amides, tosylate, hexafluorophosphate, tetrafluoroborate, bis(triflyl)amide, an alkyl, tetraphenylborate and derivatives; $X_1$ or $X_2$ can be bonded to $L_1$ or $L_2$ or to the carbene C so as to form a bidentate or chelate ligand on the ruthenium; and $L_1$, $L_2$ and $L_3$, which may be identical or different, are electron-donating ligands, such as phosphine, phosphite, phosphonite, phosphinite, arsine, stilbene, an olefin or an aromatic compound, a carbonyl compound, an ether, an alcohol, an amine, a pyridine or derivative, an imine, a thioether, or a heterocyclic carbene; $L_1$, $L_2$ or $L_3$ can be bonded to the carbene C so as to form a bidentate or chelate ligand, or a tridentate ligand.

The carbene C is represented by the general formula: $CR_1R_2$ for which $R_1$ and $R_2$ are groups which may be identical or different, such as hydrogen or any other functionalized or non-functionalized hydrocarbon-based group of saturated, unsaturated, cyclic, aromatic, branched and/or linear type. By way of examples, mention may be made of ruthenium alkylidene, benzylidene, benzylidene ether or cumylene complexes, such as vinylidenes Ru=C=CHR or allenylidenes RU=C=C=$CR_1R_2$ or indenylidenes.

A functional group (making it possible to improve the retention of the ruthenium complex in an ionic liquid) can be grafted onto at least one of the ligands $X_1$, $X_2$, $L_1$, $L_2$, or onto the carbene C. This functional group may be charged or uncharged, such as preferably an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The metathesis catalyst can optionally be rendered heterogeneous on a support in order to facilitate the recovery/recycling thereof.

The cross metathesis catalysts of the process of the invention are preferably ruthenium carbenes described, for example, in *Aldrichimica Acta*, vol 40, no 2, 2007, p. 45-52.

Examples of such catalysts are Grubbs catalysts, Hoveyda-Grubbs catalysts, Piers-Grubbs catalysts, and other metathesis catalysts of the same type, whether they are "1st generation", "2nd generation" or "3rd generation" catalysts.

Grubbs catalysts are based on a ruthenium atom surrounded by 5 ligands:
- 2 anionic ligands, such as halides;
- 2 electron-donating ligands, such as trialkyl phosphines, or saturated N-heterocyclic carbenes (called NHC ligands);
- an alkylidene group, such as substituted or unsubstituted methylene groups $=CR_2$.

These metathesis catalysts are classified into two categories, depending on the nature of their electron-donating ligands L:
- those which contain two phosphine ligands (and no saturated NHC ligand), developed first, are 1st-generation catalysts;
- those which contain a saturated NHC ligand (heterocyclic carbene) are 2nd-generation catalysts.

A type of catalyst termed "Hoveyda-Grubbs" catalyst contains, among the electron-donating ligands, a benzylidene-ether chelating ligand, and either a phosphine (1st generation) or a saturated NHC ligand (2nd generation) generally substituted with two mesityls (Mes).

Another type of catalyst termed "Piers-Grubbs" catalyst forms a four-ligand cationic complex which does not require dissociation of a ligand before the reaction.

Other types of catalysts are the "Umicore", "Zanan" and "Grela" catalysts.

Generally, the choice of the catalyst depends on the reaction under consideration.

In one embodiment, the catalyst is free of phosphine.

In one embodiment, the N-heterocyclic carbene ligand of the catalyst which may or may not be saturated is substituted with identical or different groups consisting of alkylaromatic nuclei such as phenyl, benzyl, toluyl, mesityl, benzylidene, benzhydryl, diisopropylphenyl, or mono- or di-(tert-butyl)phenyl.

Preferred catalysts are the following catalysts of formula (A) above (having ligands of SiPr type) and of formula (B) above (having ligands of SiMeS type), and in particular of formulae (A-1) to (A-10) and (B-1) to (B-5) above.

The catalyst of formula (A-1) is known under the name "M71-SIPr". The catalyst of formula (A-2) is known under the name "M72-SIPr". The catalyst of formula (A-3) is known under the name "M73-SIPr". The catalyst of formula (A-4) is known under the name "M74-SIPr". The catalyst of formula (A-5) is known under the name "Nitro-Grela-SIPr". The catalyst of formula (A-6) is known under the name "Apeiron AS2034". The catalyst of formula (A-7) is known under the name "M831-SIPr". The catalyst of formula (A-8) is known under the name "M832-SIPr". The catalyst of formula (A-9) is known under the name "M863-SIPr". The catalyst of formula (A-10) is known under the name "0711". The catalyst of formula (B-1) is known under the name "Hoveyda-Grubbs 2". The catalyst of formula (B-2) is known under the name "M51". The catalyst of formula (B-3) is known under the name "M71-SIMes". The catalyst of formula (B-4) is known under the name "Nitro-Grela-SIMes". The catalyst of formula (B-5) is known under the name "Zannan 44-0082 (Strem)".

Synthesis Process

The synthesis process according to the invention (production phase) is carried out in at least one reactor. The cross metathesis reaction is preferably carried out in liquid medium, in a solvent, in particular toluene.

The reactor initially contains a portion of the reagents, and the reaction is initiated by adding catalyst. Preferably, an additional portion of the reagents is introduced into the reactor over time. The product stream from the reactor can be withdrawn continuously or by means of partial emptying operations which are spaced out, but it is preferably withdrawn only at the end of the production phase.

The reagents and reaction products can be separated according to techniques known to those skilled in the art, such as distillation. The degraded metathesis catalyst can be recovered by adsorption, in particular on an adsorbent of silica, alumina, carbon or resin type, or by liquid extraction.

The additional reagents and the catalyst introduced throughout the reaction can be provided at predetermined instants, or else, preferably, continuously. Advantageously, the process is thus of semi-batch type, and advantageously the rate of feeding with each species is constant over time; however, the gaseous compounds produced during the reaction (such as ethylene) are continuously removed from the reactor, thus ensuring that the cross metathesis and homometathesis reactions are not equilibrium reactions, but are shifted.

Thus, typically, an initial amount of first unsaturated compound and of second unsaturated compound are introduced into the reactor. The reaction then starts when the continuous introduction of the catalyst and also of an additional second unsaturated compound stream begins. The gaseous compounds produced are continuously removed. The reaction is stopped after a certain period of time by stopping the feeding of the reactor with catalyst and with second unsaturated compound.

The gradual addition of the catalyst (preferably continuously) makes it possible to minimize the consumption thereof. Indeed, the catalyst deactivates very rapidly under the conditions of the reaction. This gradual addition also makes it possible to avoid the occurrence of an excessive concentration of light unsaturated compound (in particular ethylene) in the solution, which constitutes a poison for the reaction.

The invention provides for the use of two distinct catalysts, namely a first catalyst and then a second catalyst.

According to one preferred embodiment, the first catalyst is introduced into the reactor only for a first duration $T_1$, then the second catalyst is introduced into the reactor only for a second duration $T_2$. The introduction of the first catalyst is advantageously continuous for the duration $T_1$ (preferably with a constant feed rate) and the introduction of the second catalyst is advantageously continuous for the duration $T_2$ (preferably with a constant feed rate). The feed rates for the first catalyst and for the second catalyst may be different.

For reasons of practical implementation, there may be a transient period during which the two catalysts are introduced simultaneously during the change of catalyst.

Alternatively, it is possible to provide for:
- the injection of a first mixture of the two catalysts for the duration $T_1$ then the injection of a second mixture of the two catalysts for a duration $T_2$, the first mixture being richer in first catalyst than the second mixture; or
- the injection of the first catalyst only for the duration $T_1$ then the injection of a mixture of the two catalysts for the duration $T_2$; or
- the injection of the mixture of the two catalysts for the duration $T_1$ then the injection of the second catalyst only for the duration $T_2$; or
- a continuous modification of the composition of the stream of catalyst feeding the reactor, with a gradual enrichment with second catalyst and a gradual depletion of first catalyst.

It is also possible to provide for the introduction of more than two catalysts, and for example:

the injection of a first catalyst alone for the duration $T_1$ then the injection of a second catalyst alone for the duration $T_2$, then the injection of a third catalyst alone for an additional duration $T_3$; or the injection of a first catalyst alone for the duration $T_1$ then the injection of a mixture of two catalysts for the duration $T_2$ (in this case, this mixture of two catalysts is considered to be "the second catalyst" for the purposes of the description below); or the injection of a mixture of two catalysts for the duration $T_1$ then the injection of another catalyst for the duration $T_2$ (in this case, the mixture of two catalysts is considered to be "the first catalyst" and the other catalyst is "the second catalyst" for the purposes of the description below); and so on.

General Method for Determining the Catalyst Feed Characteristics

The invention provides for carrying out an analysis aimed at determining the catalyst feed characteristics for obtaining desired performance levels for the reaction. The analysis phase as such may or may not be integrated into the synthesis process as a preliminary step.

The aim of the analysis in question may be:
to identify, among two given catalysts, the optimal order for using the catalysts;
to choose, among a set of given catalysts, a first catalyst and a second catalyst, giving optimal results;
to determine, for a given succession of a first catalyst and of a second catalyst, the duration $T_1$ after which the changing from the first to the second catalyst is carried out.

The choice of the optimal order of two catalysts, that of an optimal pair of two catalysts, and that of an optimal duration of injection of catalyst depend on the conditions under which the synthesis is carried out (temperature, pressure, species concentrations).

Consequently, these various determinations are carried out by means of experiments carried out in "reference processes". Each reference process is carried out under the same temperature, pressure, stoichiometry and reagent-feed conditions as those of the synthesis that is envisioned.

The composition of the reaction medium is analyzed by taking samples at regular time intervals, in each reference process. This makes it possible to determine at each instant, on the one hand, the degree of conversion of the first unsaturated compound (or overall degree of conversion, ODC), which corresponds to the fraction of the first unsaturated compound having reacted, and, on the other hand, the yield of the reaction (or unitary degree of conversion, UDC) in terms of unsaturated product ($UDC_1$) and of unsaturated coproduct ($UDC_2$), this yield corresponding to the ratio of the number of moles of reagent actually converted into product (or into coproduct, and in this case there are 2 mol of reagent per mole of coproduct) to the number of moles of reagent introduced into the reaction medium. The ODC and UDC take values of between 0 and 1, limits included, i.e. between 0 and 100%.

Over time, the degree of conversion increases from 0% to a value which can reach more than 70%, or more than 75%, or more than 80%, or more than 85%, or even more than 90%. Thus, it is possible to establish the yield of unsaturated product as a function of the degree of conversion, and the yield of unsaturated coproduct as a function of the degree of conversion.

For a given pair of catalysts, the inventors have discovered that the performance levels of the synthesis process are best when the first catalyst is the one which has the higher turnover number ($TON_{TA}$) of the two, the TONs of the two catalysts being calculated in the respective reference processes, and for a given target degree of conversion $ODC_{TA}$.

The TON is defined as being the number of moles of first unsaturated compound converted per mole of catalyst. It is calculated according to the following formula $TON=C_0 \times ODC/n$ where $C_0$ represents the number of moles of first unsaturated compound introduced into the reactor and n represents the number of moles of catalyst introduced into the reactor.

The comparison of the respective catalysts is carried out for $ODC=ODC_{TA}$, which represents the target degree of conversion.

$ODC_{TA}$ can be, for example, from 30% to 95%, preferably from 40% to 90%, in particular from 50% to 80%, more particularly from 60% to 75%.

The inventors have noted that catalysts which have a high TON generally have a relatively mediocre selectivity, and vice versa.

Consequently, in the synthesis process as such, the use of the catalyst with the highest TON first makes it possible to push the conversion of the first unsaturated compound as far as possible, while minimizing catalyst consumption. Then, in a second step, the use of the catalyst with a lower TON makes it possible to correct the excesses of the first part of the process, by converting the unsaturated coproduct that was generated in relatively large amount during this first part, into the unsaturated product of interest.

The inventors have noted that, among the catalysts listed above, those corresponding to general formula (A) have a much higher TON than those corresponding to general formula (B). Consequently, it is generally advantageous to use a catalyst of formula (A) as first catalyst, then a catalyst of formula (B) as second catalyst.

Moreover, the inventors have also noted that, among the catalysts listed above, those of formulae (A-1) to (A-10) have a much higher TON than those of formulae (B-1) to (B-5). Consequently, it is generally advantageous to use a catalyst of formulae (A-1) to (A-10) as first catalyst, then a catalyst of formulae (B-1) to (B-5) as second catalyst.

As regards now the choice of an optimal pair of catalysts from a group of possible catalysts, the following are advantageously chosen:

as first catalyst, the catalyst of the group having the maximum TON in the reference process (for the target degree of conversion $ODC_{TA}$); and as second catalyst:
either the one which, among the remaining catalysts of the group, has a minimal slope factor p (and when several catalysts have equal or very close slope factors p, the one with the maximum TON is chosen);
or the one which, among the remaining catalysts of the group, has a parameter β, or according to one variant a parameter β', which is at a maximum (and when several catalysts have equal or very close parameters β', the catalyst for which a parameter γ' is minimal is chosen).

The two possible criteria for the choice of the second catalyst aim to ensure that this second catalyst is the one which allows the best possible conversion of the unsaturated coproduct.

The calculation of p, β, β' and γ' according to the results of the reference process is described in detail below in relation to a reaction example.

Finally, with regard to the duration $T_1$ after which the changing from the first to the second catalyst is carried out, it is chosen as being equal to, or as being greater than, one of two thresholds $T_{TH1}$ and $T_{TH2}$. It can, for example, be chosen as being greater than or equal to the minimum of these two thresholds, or ideally greater than or equal to the maximum of these two thresholds.

The threshold $T_{TH1}$ corresponds to the duration after which, in the reference process, the degree of conversion of the first unsaturated compound $ODC_{TH}$ and the yield in terms of unsaturated coproduct $UDC_{2TH}$ are connected by the equation $UDC_{2TH}=UDC^* \times (ODC_{TH}-1)/(ODC^*-1)$, where $UDC^*$ represents a yield in terms of unsaturated coproduct that is desired at the end of the production phase, and $ODC^*$ represents a degree of conversion of the first unsaturated compound that is desired at the end of the production phase.

The threshold $T_{TH2}$ corresponds to the duration after which, in the reference process, the second derivative of TON(t) (turnover number of the first catalyst as a function of time) is cancelled out.

Generally, the duration $T_1$ after which the changing from the first to the second catalyst is carried out is such that the degree of conversion of the first unsaturated compound is, at the end of the duration $T_1$, from 30% to 90%, preferably from 40% to 80%, and more particularly from 50% to 70%.

Method for Calculating the Parameters TON, p, β, β', γ', $T_{TH1}$ and $T_{TH2}$ The aforementioned may be understood more easily by referring to the example in which the first unsaturated compound is methyl 9-decenoate (or MD), the second unsaturated compound is acrylonitrile (ACN), the unsaturated product is methyl 10-cyano-9-decenoate (NE) and the unsaturated coproduct is methyl 9-octadecenedioate (DE).

ACN is a light compound, which has a boiling point below 100° C., whereas MD has a boiling point above 200° C.

The desired cross metathesis reaction is the reaction: ACN+MD→NE+ethylene. The ethylene produced is rapidly removed in the gas phase by entrainment with the solvent which is at its boiling point. The solvent is condensed and returned to the reactor. Owing to the continuous removal of the ethylene, the reaction is not considered to be an equilibrium reaction.

The homometathesis reaction is the reaction: MD+MD→DE+ethylene. It is also not an equilibrium reaction for the same reasons.

Another reaction which takes place is that between the ACN and the homometathesis product: ACN+DE↔MD+NE, this reaction giving again the initial reagent (MD) and the desired product (NE). This reaction is an equilibrium reaction, the desired reaction product reacting with the initial reagent to give the homometathesis product. This reverse reaction is especially present at high conversion, when the NE concentration is high, and the conversion of the MD is already well advanced.

In the reference processes, as in the synthesis processes as such, the successive catalysts are introduced continuously, and a part of the ACN is introduced before the beginning of the reaction and a part during the reaction. The gradual addition of the ACN is made necessary by the strong inhibition of the catalysts by said ACN. There cannot therefore be a high ACN content from the beginning of the reaction.

For each catalyst envisioned, a reference process is carried out, which is defined by an operating temperature and an operating pressure, and also by an initial number of moles of MD in the reactor $C_0$ and an initial number of moles of ACN in the reactor $C'_0$, and, finally, by a rate at which the reactor is fed with ACN and a rate at which the reactor is fed with catalyst.

Measurements of composition of the reaction medium over time during the reference process make it possible to determine the yields in terms of unsaturated product of interest $UDC_1$ and of unsaturated coproduct $UDC_2$ as a function of the degree of conversion ODC, as illustrated in FIG. 1.

On the basis of these measurements, it is possible to determine:
- the parameter a, which is the value of the derivative of the curve $UDC_1$ for ODC=0 (slope at the origin of the curve $UDC_1$ in the figure);
- the parameter B, which is the value of the derivative of the curve $UDC_2$ for ODC=0 (slope at the origin of the curve $UDC_2$ in the figure);
- the slope factor p (mentioned above), which corresponds to the (positive) absolute value of the derivative of the curve $UDC_2$ for ODC=1 (slope of the curve $UDC_2$ at the point ODC=1 in the figure).

With regard to the latter parameter, the experimental data collected in the reference process do not generally go up to a degree of conversion of 1 (or 100%), and it is therefore necessary to extrapolate from the shape of the curve for lower degrees of conversion.

The measurements of slopes providing the parameters a, b and p are illustrated in FIG. 1.

The turnover number of the catalyst, $TON_{T4}$, is determined according to the formula $TON_{T4}=C_0 \times ODC_{T4}/n$, where n represents the number of moles of catalysts introduced in order to carry out the reaction to the degree of conversion $ODC_{T4}$.

A parameter α can then be calculated according to the formula $\alpha=(2a/b) \times (C_0/C'_0)$.

For each experimental point, the function X can be calculated according to the following formula: $X=((UDC_2/2) \times (z/C_0-UDC_1))/((1-ODC) \times UDC_1)$, z representing the total number of moles of ACN introduced into the reaction medium at the point under consideration (including therein the initial amount $C'_0$).

For each experimental point, the function Y can also be calculated according to the following formula: $Y=((p \times \alpha)/(2+p)) \times (z/C_0-UDC_1)/UDC_1+((2+2p)/(2+p)) \times ((1-ODC)/UDC_1)$.

The function Y(X) is then approximated (adjusted) with a linear or refined model. The linear model is of the form $Y=\beta \times X$, while the refined model is of the form $Y=\beta' \times X - \gamma'$, for the experimental data obtained for the highest conversions, i.e. those obtained beyond the conversion corresponding to the maximum yield in terms of unsaturated coproduct. It is preferable to use the refined model, if the experimental data allow this.

The adjustment or approximation can be carried out, for example, using the least squares method.

As a function of all these results, it is possible to compare various catalysts according to the values of the TON and of the parameters p, β, β' and γ', as set out above.

Figure 2:
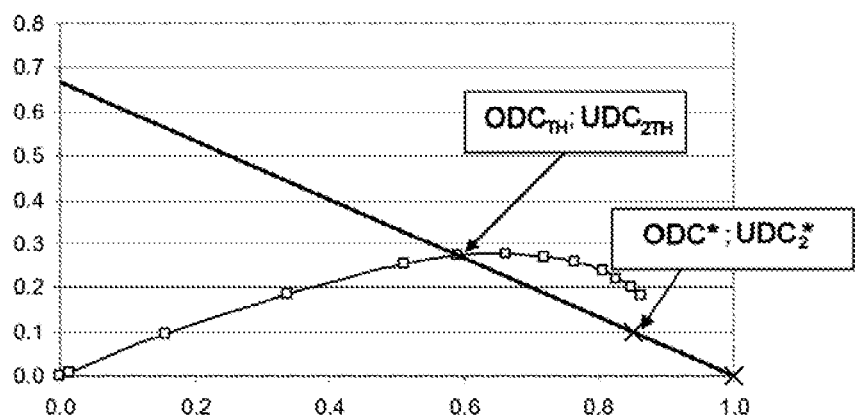
FIG. 2 is an illustration of a method for graph-based determination of a threshold duration $TTH_1$ for the introduction of the first catalyst into the reactor (on the basis of the results of FIG. 1). Reported on the figure are the point corresponding to the degree of conversion targeted at the end of the production cycle, and the targeted yield in terms of coproduct, respectively ODC* and $UDC_2$*. The point of intersection with the curve of the yield $UDC_2(ODC)$ corresponding to $[ODC_{TH}; UDG_{2TH}]$ also gives the threshold time $T_{TH1}$ corresponding to the time starting from which the catalyst permutation can be carried out.

With regard to the calculation of the threshold duration $T_{TH1}$, reference is made to FIG. 2, in which the yield in terms of coproduct $UDC_2$ as a function of the degree of conversion ODC is represented.

A degree of conversion ODC* and a yield in terms of coproduct UDC* which are desired at the end of the production phase are determined, and the line linking this point to the point [ODC=1; $UDC_2$=0] is plotted on the graph. The point of intersection [$ODC_{TH}$; $UDC_{2TH}$] between this line and the experimental curve $UDC_2$(ODC) is determined for the first catalyst under its reference conditions. The threshold duration $T_{TH1}$ corresponds to the time required to reach the degree of conversion at this point.

With regard to the determination of the threshold duration $T_{TH2}$, the curve of the TON as a function of time can be plotted and the time for which this curve exhibits a point of inflection (second derivative is cancelled out) can be measured.

The work which led to this invention received financial support from the European Union in the context of Framework Program 7 (FP7/2007-2013) under project No. 241718 EUROBIOREF.

EXAMPLES

The following examples illustrate the invention without limiting it.

Example 1

Methyl 9-Decenoate/Acrylonitrile Cross Metathesis, Reference Process

The following reaction is carried out:

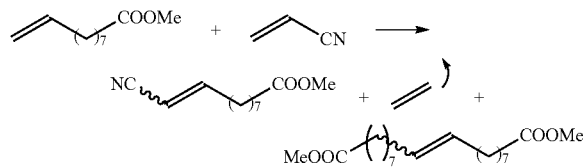

using the M71-SiPr catalyst supplied by the company Umicore.

Figure 3:
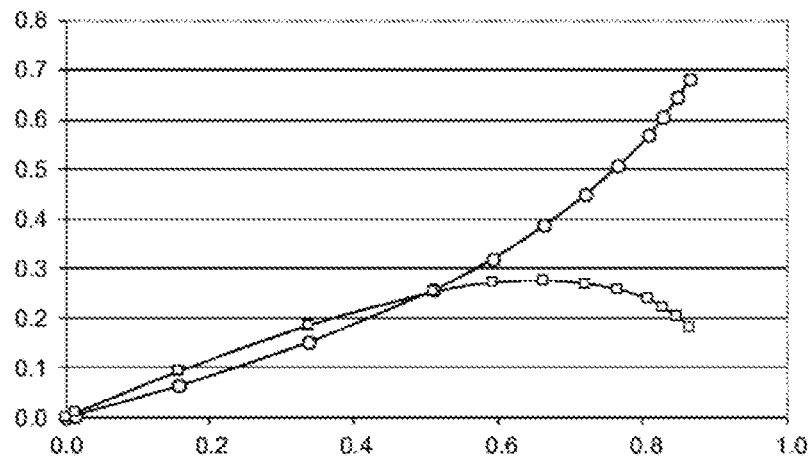
FIG. 3 is a graph showing the yield in terms of unsaturated product ($UDC_1$, points o) and of unsaturated coproduct ($UDC_2$, points □) (along the y-axis) as a function of the degree of conversion of the first unsaturated compound (along the x-axis), in the experiment of example 1 below.

15 g of methyl 9-decenoate (81.4 mmol) prepared in accordance with example 1 of document US 2011/0113679, previously passed over an alumina column, 2.15 g of acrylonitrile (40.7 mmol) and 150 g of toluene dried on molecular sieve are charged to a 250 ml glass reactor equipped with a condenser and purged with nitrogen. The mixture is heated to 110° C. and 2.6 g of acrylonitrile (49 mmol) and 2 mg of M71-SiPr catalyst ($2.44 \times 10^{-6}$ mol) dissolved in 5 g of toluene are added via syringes mounted on syringe drivers, over a period of 2 hours. Samples are taken every 30 minutes for analysis by gas chromatography. The conversions of the methyl 9-decenoate (MD) and the yields of $C_{11}$ unsaturated nitrile-ester (NE) and of $C_{18}$ unsaturated diester (DE) are reported on the graph of FIG. 3.

It is noted that, to obtain a degree of conversion of 80%, the TON is 35 800.

On the basis of the experimental results, the following values are determined for the parameters of interest:
p=1.31;
a=0.44;
b=0.56;
α=3.18.

Moreover, the linear adjustment of the function Y (X) gives the value 2.72 for the parameter β.

Example 2

Methyl 9-Decenoate/Acrylonitrile Cross Metathesis, Reference Process

The reference process is repeated for the cross metathesis between methyl 9-decenoate and acrylonitrile with another catalyst, namely the Hoveyda-Grubbs 2 catalyst (supplied by the company Aldrich).

Figure 4:
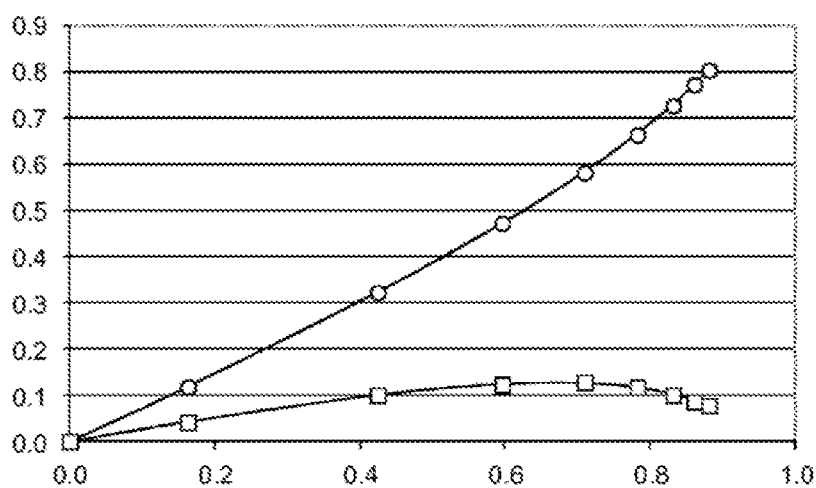
FIG. 4 is a graph showing the yield in terms of unsaturated product ($UDC_1$, points o) and of unsaturated coproduct ($UDC_2$, points □) (along the y-axis) as a function of the degree of conversion of the first unsaturated compound (along the x-axis), in the experiment of example 2 below.

15 g of methyl 9-decenoate (81.4 mmol) previously passed over an alumina column, 2.15 g of acrylonitrile (40.7 mmol) and 150 g of toluene dried on molecular sieve are charged to a 250 ml glass reactor equipped with a condenser and purged with nitrogen. The mixture is heated to 110° C. and 2.6 g of acrylonitrile (49 mmol) and 5.1 mg of Hoveyda-Grubbs 2 catalyst ($8.1 \times 10^{-6}$ mol) dissolved in 5 g of toluene are added via syringes mounted on syringe drivers, over a period of 2 hours. Samples are taken every 15 minutes for analysis by gas chromatography. The conversions of the methyl 9-decenoate (MD) and the yields of $C_{11}$ unsaturated nitrile-ester (NE) and of the $C_{18}$ unsaturated diester (DE) are reported on the graph of FIG. 4.

It is noted that, to obtain a degree of conversion of 80%, the TON is 12 600.

On the basis of the experimental results, the following values are determined for the parameters of interest:
p=0.63;
a=0.78;
b=0.24;
α=12.89.

Moreover, the linear adjustment of the function Y (X) gives the value 16.2 for the parameter β.

Example 3

Methyl 9-Decenoate/Acrylonitrile Cross Metathesis, Process According to the Invention The cross metathesis reaction is carried out using successively the M71-SiPr catalyst and then the Hoveyda-Grubbs 2 catalyst, under the same conditions as examples 1 and 2.

15 g of methyl 9-decenoate (81.4 mmol) previously passed over an alumina column, 2.15 g of acrylonitrile (40.7 mmol) and 150 g of toluene dried on molecular sieve are charged to a 250 ml glass reactor equipped with a condenser and purged with nitrogen. The mixture is heated to 110° C. and 1.3 g of acrylonitrile (25 mmol) and 1 mg of M71-SiPr catalyst ($1.22 \times 10^{-6}$ mol) dissolved in 5 g of toluene are added via syringes mounted on syringe drivers, over a period of 1 hour.

The reaction is then continued by adding, over a period of 1 hour, 1.3 g of acrylonitrile (25 mmol) and 1.5 mg of Hoveyda-Grubbs 2 catalyst ($2.45 \times 10^{-6}$ mol) dissolved in 5 g of toluene.

Figure 5:
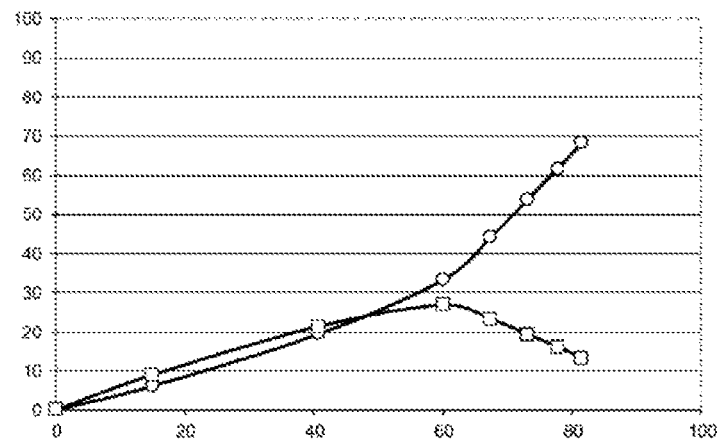
FIG. 5 is a graph showing the yield in terms of unsaturated product ($UDC_1$, points o) and of unsaturated coproduct ($UDC_2$, points □) (along the y-axis) as a function of the degree of conversion of the first unsaturated compound (along the x-axis), in the experiment of example 3 below.

The conversions of the methyl 9-decenoate (MD) and the yields of $C_{11}$ unsaturated nitrile-ester (NE) and of the $C_{18}$ unsaturated diester (DE) are reported on the graph of FIG. 5.

Compared with the M71-SiPr catalyst alone, this example shows that it is possible to reduce the final yield of diester (12% compared with 18% in the reference test).

Compared with the Hoveyda-Grubbs 2 catalyst alone, this test shows that it is possible to use less catalyst (45 mol ppm compared with 100 ppm) in the reference test in order to obtain similar diester yields.

Example 4

Methyl 9-Decenoate/Acrylonitrile Cross Metathesis (Comparative)

The cross metathesis reaction is carried out using successively the Hoveyda-Grubbs 2 catalyst and then the M71-SiPr catalyst, under the same conditions as examples 1 and 2.

15 g of methyl 9-decenoate (81.4 mmol) previously passed over an alumina column, 2.15 g of acrylonitrile (40.7 mmol) and 150 g of toluene dried on molecular sieve are charged to a 250 ml glass reactor equipped with a condenser and purged with nitrogen. The mixture is heated to 110° C. and 1.3 g of acrylonitrile (25 mmol) and 1.5 mg of Hoveyda-Grubbs 2 catalyst ($2.45 \times 10^{-6}$ mol) dissolved in 5 g of toluene are added via syringes mounted on syringe drivers, over a period of 1 hour.

The reaction is then continued by adding, over a period of 1 hour, 1.3 g of acrylonitrile (25 mmol) and 1 mg of M71-SiPr catalyst ($1.22 \times 10^{-6}$ mol) dissolved in 5 g of toluene.

Figure 6:
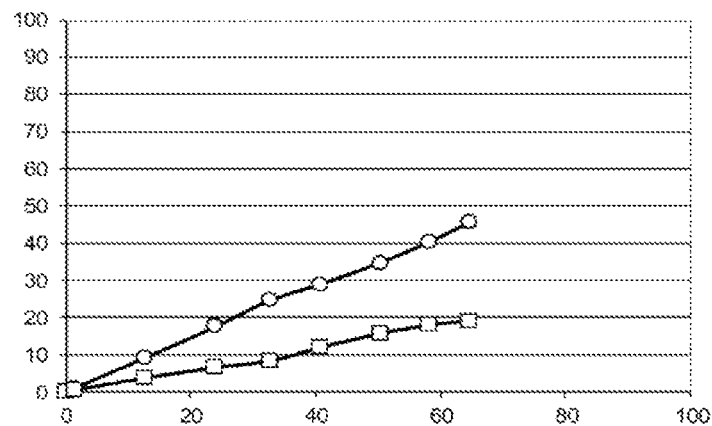
FIG. 6 is a graph showing the yield in terms of unsaturated product ($UDC_1$, points o) and of unsaturated coproduct ($UDC_2$, points □) (along the y-axis) as a function of the degree of conversion of the first unsaturated compound (along the x-axis), in the experiment of example 4 below.

The conversions of the methyl 9-decenoate (MD) and the yields of $C_{11}$ unsaturated nitrile-ester (NE) and of the $C_{18}$ unsaturated diester (DE) are reported on the graph of FIG. 6.

Example 5

Methyl 9-Decenoate/Acrylonitrile Cross Metathesis (Comparative)

The cross metathesis reaction is carried out using simultaneously the M71-SiPr and Hoveyda-Grubbs 2 catalysts, under the same conditions as examples 1 and 2.

15 g of methyl 9-decenoate (81.4 mmol) previously passed over an alumina column, 2.15 g of acrylonitrile (40.7 mmol) and 150 g of toluene dried on molecular sieve are charged to a 250 ml glass reactor equipped with a condenser and purged with nitrogen. The mixture is heated to 110° C. and 2.6 g of acrylonitrile (25 mmol), 1 mg of M71-SiPr catalyst ($1.22 \times 10^{-6}$ mol) and 1.5 mg of Hoveyda-Grubbs 2 catalyst ($2.45 \times 10^{-6}$ mol) dissolved in 5 g of toluene are added via syringes mounted on syringe drivers, over a period of 2 hours.

Figure 7:
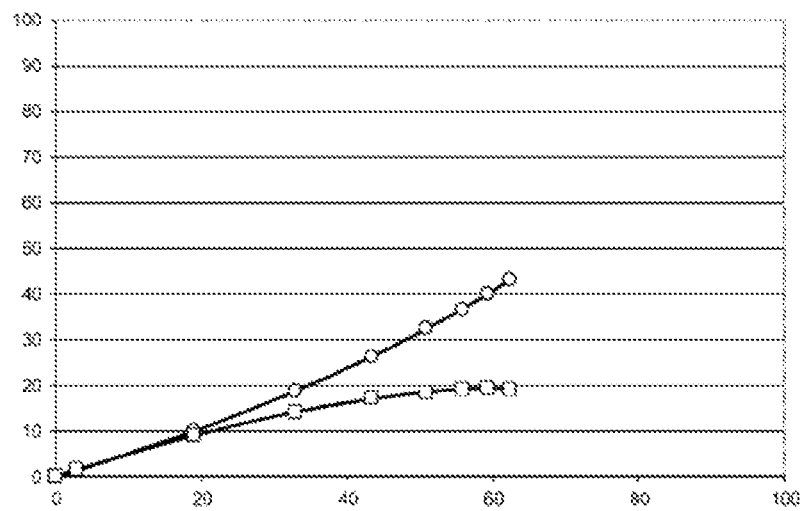
FIG. 7 is a graph showing the yield in terms of unsaturated product ($UDC_1$, points o) and of unsaturated coproduct ($UDC_2$, points o) (along the y-axis) as a function of the degree of conversion of the first unsaturated compound (along the x-axis), in the experiment of example 5 below.

The conversions of the methyl 9-decenoate (MD) and the yields of $C_{11}$ unsaturated nitrile-ester (NE) and of the $C_{18}$ unsaturated diester (DE) are reported on the graph of FIG. 7.

The invention claimed is:

1. A process for the synthesis of an unsaturated product by cross metathesis between a first unsaturated compound comprising at least 8 carbon atoms and a second unsaturated compound comprising less than 8 carbon atoms, the first unsaturated compound being capable of producing an unsaturated coproduct comprising more than 14 carbon atoms, by homometathesis, said process comprising at least one production phase which comprises:
   feeding a reactor with the first unsaturated compound;
   feeding the reactor with the second unsaturated compound;
   feeding the reactor with at least a first metathesis catalyst, then feeding the reactor with at least a second metathesis catalyst;
   withdrawing a product stream arising from the reactor;
   a turnover number of the first catalyst being higher than a turnover number of the second catalyst so as to achieve a same target degree of conversion of the first unsaturated compound, the turnover numbers of the catalysts being determined under temperature, pressure, stoichiometry and reagent concentration conditions identical to those of the production phase.

2. The process as claimed in claim 1, wherein the same target degree of conversion is from 30% to 95%.

3. The process as claimed in claim 1, wherein the production phase is semi-batch, and comprises successively:
   (1) feeding the reactor with all of the first unsaturated compound and a first part of the second unsaturated compound, before starting up the reaction;
   (2) gradually feeding the reactor with a second part of the second unsaturated compound and with the first catalyst;
   (3) gradually feeding the reactor with a third part of the second unsaturated compound and with the second catalyst.

4. The process as claimed in claim 1, wherein:
   the first unsaturated compound has the formula:

   $$R_1-CH=CH-(CH_2)_n-R_2; \quad (I)$$

the second unsaturated compound has the formula:

   $$R_3-CH=CH-R_4; \quad (II)$$

the unsaturated product has the formula:

   $$R_4-CH=CH-(CH_2)_n-R_2; \quad (III)$$

the unsaturated coproduct has the formula:

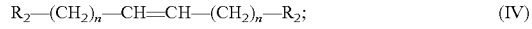
   $$R_2-(CH_2)_n-CH=CH-(CH_2)_n-R_2; \quad (IV)$$

$R_1$ representing a hydrogen atom or an alkyl or alkenyl radical comprising from 1 to 8 carbon atoms;
   $R_2$ representing $COOR_5$ or CN or CHO or $CH_2OH$ or $CH_2Cl$ or $CH_2Br$;
   $R_3$ and $R_4$ each representing a hydrogen atom or an alkyl radical comprising from 1 to 4 carbon atoms or $COOR_5$ or CN or CHO or $CH_2OH$ or $CH_2Cl$ or $CH_2Br$, $R_3$ and $R_4$ being identical or different and not comprising in total more than 6 carbon atoms;
   $R_5$ representing a hydrogen atom or an alkyl radical comprising from 1 to 4 carbon atoms; and n being an integer from 4 to 11.

5. The process as claimed in claim 1, wherein:
   the second unsaturated compound is an acrylate or acrylonitrile,
   the first unsaturated compound is an acid, an unsaturated nitrile or an unsaturated ester, the unsaturated product is an unsaturated nitrile-ester, nitrile-acid, dinitrile or diester, and
   the unsaturated coproduct is an unsaturated diester, dinitrile or diacid.

6. The process as claimed in claim 1, wherein the metathesis reactions are carried out in a liquid phase, where appropriate in a solvent.

7. The process as claimed in claim 1, wherein a degree of conversion of the first unsaturated compound at the end of the production phase is from 50% to 98.

8. The process as claimed in claim 1, comprising a preliminary phase of selecting the first catalyst and the second catalyst from a set of possible catalysts, before the production phase.

9. The process as claimed in claim 8, wherein the preliminary selection phase comprises:
   carrying out a reference process for each possible catalyst, each reference process comprising feeding the reactor with the first unsaturated compound, feeding the reactor with the second unsaturated compound and feeding the reactor with the catalyst, the temperature, pressure, stoichiometry and reagent concentration conditions for each reference process being identical to those used for the production phase;

collecting the results of the reference processes, comprising measuring concentrations of chemical species in the reactor over time;

choosing the first catalyst and the second catalyst according to the results of the reference processes.

10. The process as claimed in claim 9, wherein the first catalyst is the catalyst which has a maximum turnover number in the reference process, for a same target degree of conversion of the first unsaturated compound.

11. The process as claimed in claim 9, wherein the second catalyst is a catalyst for which, in the reference process, an absolute value of the derivative of the yield of the reaction in terms of unsaturated coproduct, as a function of a degree of conversion of the first unsaturated compound, determined at a degree of conversion of 1, is minimal.

12. The process as claimed in claim 11, wherein the second catalyst is chosen, from the catalysts for which, in the reference process, an absolute value of the derivative of the yield of the reaction in terms of unsaturated coproduct, as a function of a degree of conversion of the first unsaturated compound, measured at a degree of conversion of 1, is minimal, as being the catalyst for which a turnover number in the reference process is at a maximum, for a same target degree of conversion of the first unsaturated compound.

13. The process as claimed in claim 9, wherein:

a number X is calculated at various instants of each reference process, said number X being defined by the following formula:

$$X=(UDC_2/2)\times(z/C_0-UDC_1)/((1-ODC)\times UDC_1), \quad (1)$$

in which $C_0$ represents the number of moles of the first unsaturated compound in the reactor before the beginning of feeding with catalyst, ODC represents a degree of conversion of the first unsaturated compound at the instant under consideration, $UDC_1$ represents the yield of the reaction in terms of unsaturated product at the instant under consideration, $UDC_2$ represents the yield of the reaction in terms of unsaturated coproduct at the instant under consideration, and z represents the cumulative total number of moles of second unsaturated compound that are introduced into the reactor at the instant under consideration;

a number Y is calculated at various instants of each reference process, said number Y being defined by the following formula:

$$Y=(p\times\alpha(2+p)\times(z/(C_0\times UDC_1)-1)+(2+2p)\times(1-ODC)/((2+p)\times UDC_1) \quad (2)$$

in which $C_0$, ODC, $UDC_1$ and z have the meaning above, p represents the absolute value of the derivative of the function $UDC_2(ODC)$ for a degree of conversion equal to 1, and $\alpha$ is $(2a/b)\times(C_0/C'_0)$, a representing the derivative of the function $UDC_1(ODC)$ for a degree of conversion equal to 0, b representing the derivative of the function $UDC_2(ODC)$ for a degree of conversion equal to 0 and $C'_0$ representing the number of moles of the second unsaturated compound in the reactor before the beginning of feeding with catalyst;

the function Y(X) is approximated by an equation $Y=\beta\times X$ or by an equation $$Y=\beta'\times X-\gamma';$$

the second catalyst is selected as being the catalyst for which the parameter $\beta$ or $\beta'$ is at a maximum.

14. The process as claimed in claim 1, wherein the reactor is fed with first catalyst until a degree of conversion of the first unsaturated compound reaches a threshold value, said threshold value being from 30% to 90%.

15. The process as claimed in claim 1, wherein the reactor is fed with first catalyst for a duration equal to, or greater than, a threshold duration, said threshold duration being that after which a degree of conversion of the first unsaturated compound $ODC_{TH}$ and the yield in terms of unsaturated coproduct $UDC_{2TH}$ in a reference process, are connected by the equation $UDC_{2TH}=UDC^*\times(ODC_{TH}-1)/(ODC^*-1)$, where $UDC^*$ is the value of the yield in terms of unsaturated coproduct that is desired at the end of the production phase, and $ODC^*$ is the value of the degree of conversion of the first unsaturated compound that is desired at the end of the production phase, the reference process comprising feeding the reactor with the first unsaturated compound, feeding the reactor with the second unsaturated compound and feeding the reactor with the first catalyst, the temperature, pressure, stoichiometry and reagent concentration conditions for the reference process being identical to those used during the production phase.

16. The process as claimed in claim 1, wherein the reactor is fed with first catalyst for a duration equal to, or greater than, a threshold duration which is the duration after which, in a reference process, the second derivative of a turnover number of the first catalyst as a function of time is cancelled out, the reference process comprising:

feeding the reactor with the first unsaturated compound, feeding the reactor with the second unsaturated compound and feeding the reactor with the first catalyst, the temperature, pressure, stoichiometry and reagent concentration conditions for the reference process being identical to those used during the production phase.

17. The process as claimed in claim 1, comprising, before the production phase, a preliminary phase for determining the duration of introduction of the first catalyst, which comprises:

carrying out the reference process;

collecting results of a reference process, comprising measuring concentrations of chemical species in the reactor over time; and calculating a duration of introduction of the first catalyst according to results of the reference processes.

18. The process as claimed in claim 1, wherein the first catalyst and/or the second catalyst are ruthenium-carbene catalysts chosen from the catalysts of formulae (A) and (B) below:

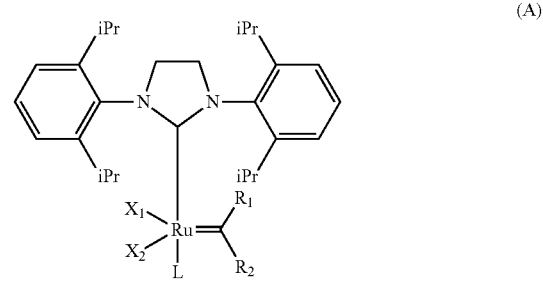

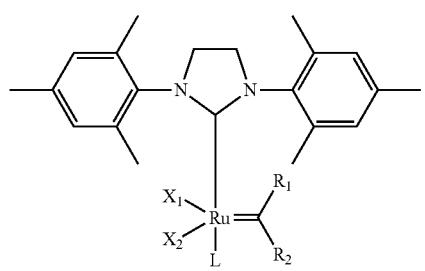

(B)

in which $X_1$ and $X_2$ are anionic ligands,

L is an electron-donating neutral ligand, and $R_1$ and $R_2$ represent H or a substituent containing from 1 to 20 carbon atoms of alkyl, alkenyl, alkynyl, aryl, alkoxy, alkenyloxy, alkynyloxy, aryloxy, alkoxycarbonyl, alkylthiol, arylthiol, alkylsulfonyl or alkylsulfinyl type; the substituent optionally containing groups of hydroxyl, thiol, thioether, ketone, aldehyde, ester, ether, amine, imine, amide, nitro, carboxylic acid, disulfide, carbonate, isocyanate, carbodiimide, carboalkoxy, carbamate or halogen type.

19. The process as claimed in claim 1, wherein the first catalyst and/or the second catalyst are chosen from the catalysts of formulae (A-1) to (A-10) and (B-1) to (B-5) below:

(A-1)

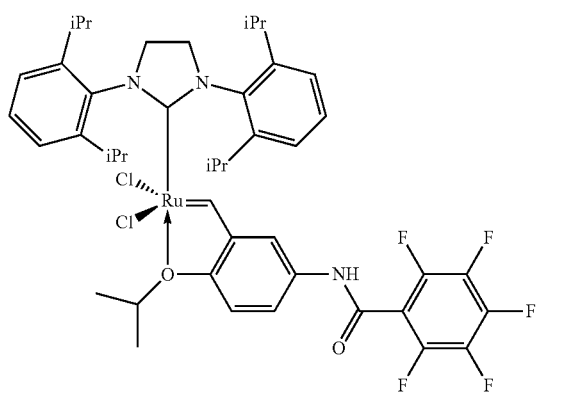

(A-2)

(A-3)

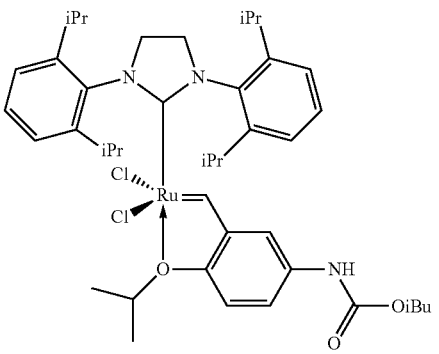

(A-4)

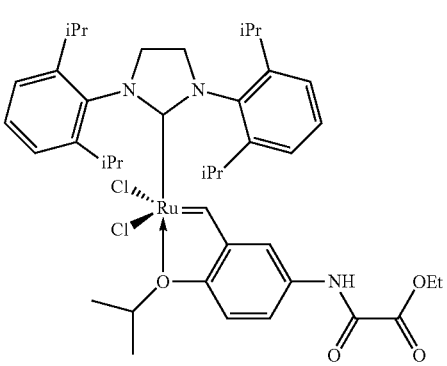

(A-5)

(A-6)

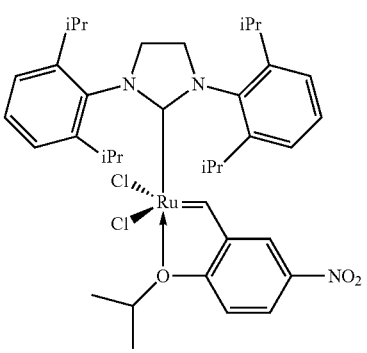

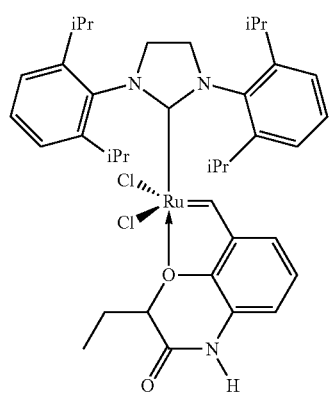 (A-7)
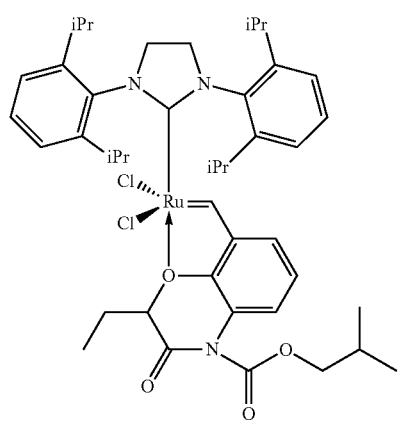 (A-8)
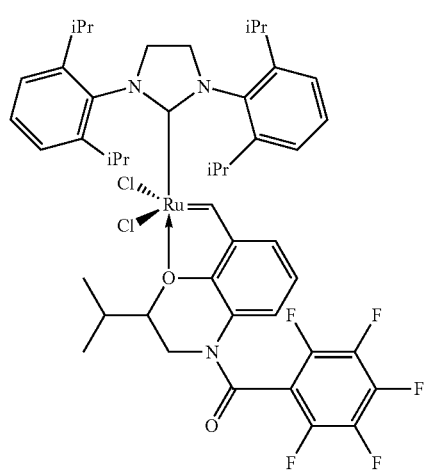 (A-9)
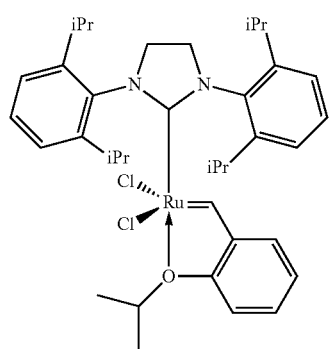 (A-10)
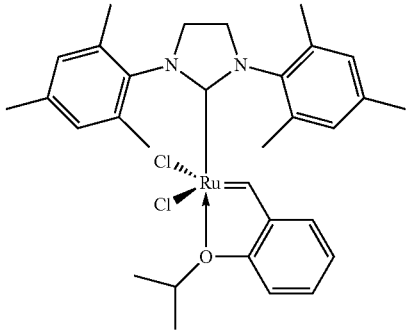 (B-1)
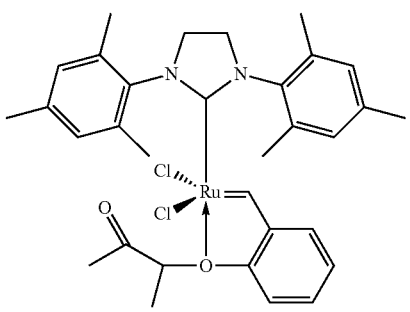 (B-2)
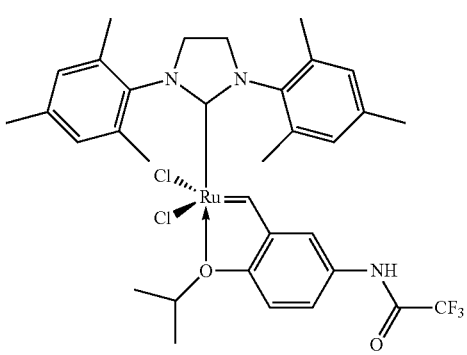 (B-3)
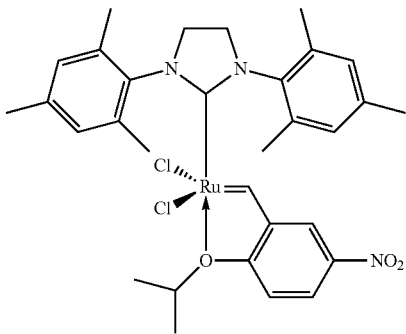 (B-4)

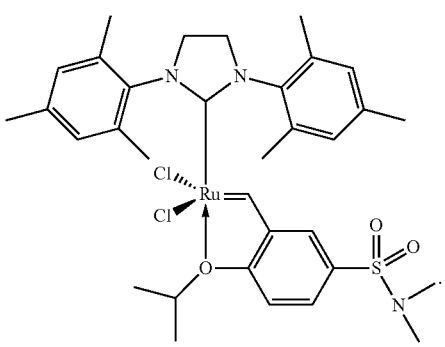

20. The process as claimed in claim 1, wherein:
the first catalyst is a catalyst of formula (A)

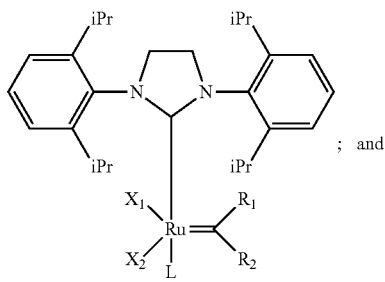

(A)

the second catalyst is a catalyst of formula (B)

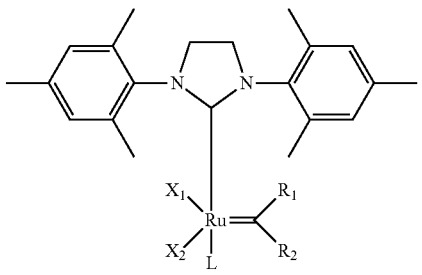

(B)

(B-5)

in which $X_1$ and $X_2$ are anionic ligands

L is an electron-donating neutral ligand, and $R_1$ and $R_2$ represent H or a substituent containing from 1 to 20 carbon atoms of alkyl, alkenyl, alkynyl, aryl, alkoxy, alkenyloxy, alkynyloxy, aryloxy, alkoxycarbonyl, alkylthiol, arylthiol, alkylsulfonyl or alkylsulfinyl type; the substituent optionally containing groups of hydroxyl, thiol, thioether, ketone, aldehyde, ester, ether, amine, imine, amide, nitro, carboxylic acid, disulfide, carbonate, isocyanate, carbodiimide, carboalkoxy, carbamate or halogen type.

21. A process for the synthesis of an α,ω-aminoalkanoic acid or ester, comprising:

synthesis of an unsaturated product by cross metathesis between a first unsaturated compound comprising at least 8 carbon atoms and a second unsaturated compound comprising less than 8 carbon atoms, the first unsaturated compound being capable of producing an unsaturated coproduct comprising more than 14 carbon atoms, by homometathesis, said process comprising at least one production phase which comprises:

feeding a reactor with the first unsaturated compound;

feeding the reactor with the second unsaturated compound;

feeding the reactor with at least a first metathesis catalyst, then feeding the reactor with at least a second metathesis catalyst;

withdrawing a product stream arising from the reactor;

a turnover number of the first catalyst being higher than a turnover number of the second catalyst so as to achieve a same target degree of conversion of the first unsaturated compound, the turnover numbers of the catalysts being determined under temperature, pressure, stoichiometry and reagent concentration conditions identical to those of the production phase, wherein the unsaturated product is an unsaturated nitrile-ester or nitrile-acid, and a reaction for hydrogenation thereof.

\* \* \* \* \*